US010011823B2

(12) United States Patent
Barbieri et al.

(10) Patent No.: US 10,011,823 B2
(45) Date of Patent: Jul. 3, 2018

(54) ENGINEERED BOTULINUM NEUROTOXIN

(75) Inventors: Joseph T. Barbieri, Milwaukee, WI (US); Sheng Chen, Hung Hom (HK)

(73) Assignee: MEDICAL COLLEGE OF WISCONSIN, INC., Milwaukee, WI (US)

( * ) Notice: Subject to any disclaimer, the term of this patent is extended or adjusted under 35 U.S.C. 154(b) by 0 days.

(21) Appl. No.: 13/264,078

(22) PCT Filed: Apr. 13, 2010

(86) PCT No.: PCT/US2010/030875
§ 371 (c)(1), (2), (4) Date: Oct. 12, 2011

(87) PCT Pub. No.: WO2010/120766
PCT Pub. Date: Oct. 21, 2010

(65) Prior Publication Data

US 2012/0039941 A1 Feb. 16, 2012

Related U.S. Application Data

(60) Provisional application No. 61/169,031, filed on Apr. 14, 2009.

(51) Int. Cl.

| | |
|---|---|
| ***C12N 9/52*** | (2006.01) |
| ***C07K 14/33*** | (2006.01) |
| ***A61P 35/00*** | (2006.01) |
| ***A61P 11/00*** | (2006.01) |
| ***A61P 29/00*** | (2006.01) |
| ***A61P 37/00*** | (2006.01) |
| ***A61K 39/08*** | (2006.01) |
| ***A61P 11/06*** | (2006.01) |
| *A61K 38/00* | (2006.01) |

(52) U.S. Cl.
CPC ................ *C12N 9/52* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 2004/0115727 A1 | 6/2004 | Steward et al. | | |
| 2006/0211619 A1 | 9/2006 | Steward et al. | | |
| 2008/0096248 A1* | 4/2008 | Steward et al. | ............. | 435/69.1 |
| 2008/0161543 A1* | 7/2008 | Steward et al. | .............. | 530/402 |

OTHER PUBLICATIONS

Bowie et al (Science, 1990, 257:1306-1310).*
Chen, et al., Multiple Pocket Recognition of SNAP25 by Botulinum Neurotoxin Serotype E, Journal of Biological Chemistry, 2007, 282(35):25540-25547.
Foster, et al., Re-engineering the Target Specificity of Clostridial Neurotoxins—A Route to Novel Therapeutics, Neurotoxicity Research, 2006, 9(2,3):101-107.
Holt, et al., Identification of SNAP-47, A Novel Qbc-SNARE with Ubiquitous Expression, Journal of Biological Chemistry, 2006, 281(25):17076-17083.
Oyler, et al., The Identification of a Novel Synaptosomal-Associated Protein, SNAP-25, Differentially Expressed by Neuronal Subpopulations, Journal of Cell Biology, 1989, 109:3039-3052.
Sadoul, et al., SNAP-23 Is Not Cleaved by Botulinum Neurotoxin E and Can Replace SNAP-25 in the Process of Insulin Secretion, Journal of Biological Chemistry, 1997, 272(52):33023-33027.
Vaidyanathan, et al., Proteolysis of SNAP-25 Isoforms by Botulinum Neurotoxin Types A, C, and E: Domains and Amino Acid Residues Controlling the Formation of Enzyme-Substrate Complexes and Cleavage, Journal of Neurochemistry, 1999, 72(1):327-337.
International Search Report and Written Opinion dated Sep. 17, 2010 in connection with PCT/US2010/030875.
Kukreja et al. Role of two active site Glu residues in the molecular action of botulinum neurotoxin endopeptidase; Biochimica et Biophysica Acta 2007; 1774:213:222.
Chen, et al. Unique Substrate Recognition by Botulinum Neurotoxins Serotypes A and E; The Journal of Biological Chemistry 2006; 281(16):10906-10911.
Montal; Botulinum Neurotoxin: A Marvel of Protein Design; Ann. Rev. Biochem. E-Pub Mar. 16, 2010; 79:591-617.
Chen et al.; Engineering botulinum neurotoxin to extend therapeutic intervention; PNAS Jun. 9, 2009; 106(23):9180-9184.
S.M. Whelan, et al., "The complete amino acid sequence of the Clostridium botulinum type-E neurotoxin, derived by nucleotide-sequence analysis of the encoding gene". Eur. J. Biochem., 1992, 204: 654-667, FEBS.
Agarwal, et al., Analysis of Active Site Residues of Botulinum Neurotoxin E by Mutational, Functional, and Structural Studies: Glu335Gln Is an Apoenzyme, Biochemistry, 2005, 44(23):8291-8302.
"Patent Examination Report No. 1," issued in related Australian Patent Application No. 2010236613 (dated Jan. 5, 2015).
"Communication pursuant to Article 94(3) EPC," issued in related European Application No. EP 10 765 009.5 (dated Apr. 1, 2015).

* cited by examiner

*Primary Examiner* — Robert A Zeman
(74) *Attorney, Agent, or Firm* — Maier & Maier, PLLC

(57) ABSTRACT

The present invention provides a novel modified BoNT/E catalytic domain and methods of use thereof. In one embodiment, the light chain residue 224, or a residue corresponding to residue 224, of the modified BoNT/E catalytic domain has been altered to be aspartic acid or glutamic acid. The modified catalytic domain cleaves SNAP23 but does not cleave SNAP29 or SNAP47, providing novel methods of treating diseases including without limitation, asthma, CF, chronic obstructive pulmonary, gastric acid efflux and inflammation, immune disorders with a cytokine component or cancers with a cytokine component.

3 Claims, 6 Drawing Sheets

(a)

(b)

| LC/Es | Substrate | $K_m$ (μM) | $K_{cat}$ ($S^{-1}$) | $K_{cat}/K_m$ ($S^{-1}μM^{-1}$) |
|---|---|---|---|---|
| WT | SNAP25 | 1.6 ± 0.3 | 77 | 50.0 |
| $K^{224}D$ | SNAP23 | 3.3 ± 0.9 | 17 | 5.4 |

ENGINEERED BOTULINUM NEUROTOXIN

CROSS-REFERENCE TO RELATED APPLICATIONS

This application claims priority to PCT International Application No. PCT/US2010/030875 filed Apr. 13, 2010 and U.S. Provisional Application 61/169,031, filed Apr. 14, 2009, both of which are hereby incorporated by reference for all purposes.

STATEMENT REGARDING FEDERALLY-SPONSORED RESEARCH OR DEVELOPMENT

This invention was made with United States government support awarded by the following agency: NIH grant 1-U54-AI-057153. The United States government has certain rights in this invention.

BACKGROUND OF THE INVENTION

*Clostridium botulinum* produces seven different neurotoxins (BoNTs) which differentiated serologically by the lack of anti-serum cross serotype neutralization. BoNTs are the most potent toxins known to humans and are the causative agents of the disease botulism (1). BoNTs exert their action by inhibiting the release of the neurotransmitter acetylcholine at the neuromuscular junction, leading to a state of flaccid paralysis. BoNTs elicit neuronal-specific flaccid paralysis by targeting neurons and cleaving neuron specific SNARE proteins.

SNARE proteins (Soluble NSF Attachment protein Receptors) are a large superfamily of proteins. The main function of SNARE proteins is to mediate the exocytosis of neurotransmitter molecules to the post-synaptic junction. SNAREs are small, abundant and both vesicle and plasma-membrane bound proteins.

BoNTs are a 150 kDa polypeptide chain comprising a 100 kDa heavy chain and a 50 kDa light chain linked by a disulfide bond. BoNTs are organized into three functional domains: an N-terminal zinc metalloprotease light chain (LC), a translocation domain (HCT) and a C-terminal receptor binding domain (HCR) (1, 2). The toxic effect of BoNTs (nerve intoxification) is accomplished through the interplay of three key events. One, the carboxy half of the heavy chain is required for receptor-specific binding to cholinergic nerve cells at the nerve-cell membrane. After binding, another portion of the BoNT moves a smaller catalytic domain into the cell, where the catalytic domain binds to and cleaves a neuronal SNARE protein, "intoxicating" the nerve cell, making it impossible to "fire" or send signals. By "catalytic domain" we mean the part of the molecule that triggers the cleavage of the substrate. The toxin is internalized into an endosome through receptor-mediated endocytosis, and the toxin binds the liminal domains of synaptic vesicle-associated proteins upon the fusion of synaptic vesicles with the plasma membrane (3-5). In short, BoNTs are internalized into endosomes and upon acidification, the LC is translocated into the cytoplasm, where SNARE proteins are cleaved (1, 2).

Mammalian neuronal exocytosis is driven by the formation of protein complexes between the vesicle SNARE, VAMP2, and the plasma member and SNAREs, SNAP 25 and syntaxin 1a (6). There are seven serotypes of BoNTs (termed A-G) that cleave specific residues on one of three SNARE proteins: serotypes B, D, F, and G cleave VAMP-2, serotypes A and E cleave SNAP 25, and serotype C cleaves SNAP 25 and syntaxis 1a (1). Thus, neuronal specificity is based upon BoNT binding to neurons and cleaving neuronal isoforms of the SNARE proteins. For example, BoNT/A cleaves human SNAP25, but not the human non-neuronal isoform SNAP 23 (7, 8). The non-neuronal SNARE isoforms are involved in a divergent cellular processes, including fusion reactions in cell growth, membrane repair, cytokinesis and synaptic transmission.

The reversible nature of muscle function after BoNTs intoxication that replace toxin-affected nerves with new nerves (10, 11), has turned the BoNTs from a deadly agent to novel therapies for neuromuscular conditions. As early as 1989, BoNT/A was approved by the FDA to treat strabismus, blepharospasm, and hemifacial spasm and then for cervical dystonia, cosmetic use, glabellar facial lines and axillary hyperhidrosis (12). BoNT/A efficacy in dystonia and other disorders related to involuntary skeletal muscle activity, coupled with a satisfactory safety profile, and prompted empirical/off-label use in a variety of secretions and pain and cosmetic disorders (13).

The clinical use of BoNTs is limited to targeting inflictions affecting neuromuscular activity (12, 13). Elucidation of the structure-function relationship of BoNTs has enabled the design of novel therapies that retarget BoNT to unique neurons and non-neuronal cells. Replacement of BoNT HCR domain with nerve growth factor, lectin from *Erythrina cristagalli*, or epidermal growth factors enable retargeting of BoNT/A to neuronal or non-neuronal cells such as nociceptive afferents and airway epithelium cells (14-16). However, the selective cleavage of neuronal specific SNARE proteins by BoNT has limited development of novel therapies in these non-neuronal systems. Prerequisite to develop novel therapies requires the retargeting of the catalytic activity of the BoNTs to non-neuronal SNARE isoforms.

Accordingly, a need exists for an engineered BoNT that cleaves non-neuronal SNARE proteins and methods of use thereof.

SUMMARY OF THE INVENTION

In one embodiment, the present invention provides a modified BoNT/E catalytic domain, wherein light chain residue 224, or a residue corresponding to residue 224, has been altered. In one embodiment, the residue 224 has been altered to be aspartic acid or glutamic acid. The modified catalytic domain cleaves SNAP23 but does not cleave SNAP29 or SNAP47.

In an alternate embodiment, the modified catalytic domain additionally comprise a target molecule useful in a protein delivery system.

In an alternate embodiment, the present invention provides an engineered botulinum neurotoxin E or botulinum neurotoxin light chain or botulinum toxin catalytic domain comprising a modified BoNT/E catalytic domain, wherein light chain residue 224 has been altered.

In an alternate embodiment, the present invention provides a method of treating a subject in need of botulinum toxin therapy, comprising the step of administering a therapeutically effective amount of a modified BoNT/E catalytic domain, wherein light chain residue 224 has been altered, to the subject. The subject in need of botulinum toxin therapy may suffer from, without limitation, asthma, CF, chronic obstructive pulmonary, gastric acid efflux and inflammation, immune disorders with a cytokine component or cancers with a cytokine component.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION OF THE INVENTION

I. In General

Figure 1:
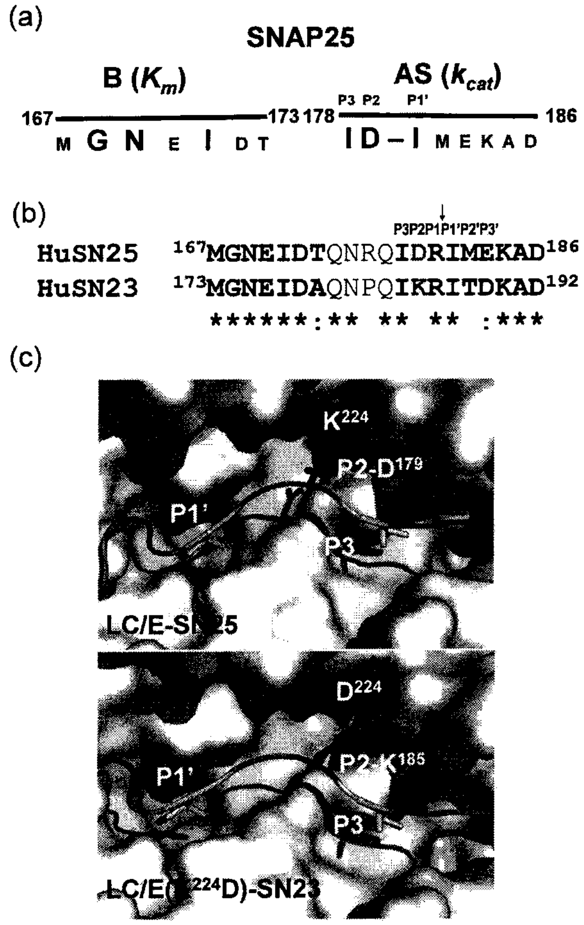
FIG. 1. $K^{185}$ of human SNAP23 contributes to the substrate recognition by BoNT/E. (a) Substrate recognition by LC/E. Two subsites in SNAP25 contribute to substrate binding "B" ($K_m$) and catalysis "AS" ($k_{cat}$), where the P3, P2, and PI' residues contribute to recognition by LC/E. (b) Sequence alignment of human SNAP25 (SN25) (SEQ ID NO: 9) and human SNAP23 (SN23) (SEQ ID NO: 10). (c) (upper panel) modeled complex structure of LC/ESNAP25 predict the recognition of P site residues of SNAP25 by LC/E. (lower panel) modeled complex structure of LC/E($K^{224}$D)-SNAP23 predict the recognition of P site residues of SNAP23 by LC/E($K^{224}$D). Models were generated by SWISS-MODEL, using LC/E crystal structure (PDB:3d3x), and images were generated in PyMol.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention provides novel engineered botulinum neurotoxins (BoNTs) that cleave non-neuronal SNARE proteins and methods of use thereof.

BoNTs are effective therapeutics for a variety of neurological disorders, such as strabismus, blepharospasm, hemificial spasm, and cervical dystonia, due to the toxin's tropism for neurons and specific cleavage of neuronal SNARE proteins. Modifying BoNTs to bind non-neuronal cells requires retargeting the catalytic activity of BoNTs to non-neuronal SNARE isoforms to provide effective non-neuronal therapies.

Here, we extend the substrate specificity of BoNT/E by engineering a catalytic derivative that cleaves the non-neuronal SNARE protein, SNAP23, as a platform for novel methods of treating non-neuronal human secretory diseases. By "non-neuronal human secretory diseases, we mean, for example, diseases or conditions where excessive airway mucus secretion, mucus hypersecretion, may cause mucus accumulation that is associated with human clinical conditions such as asthma and chronic obstructive pulmonary disease where mucus accumulation contributes to respiratory disease. Specifically, we now report for the first time the engineering of a BoNT/E derivative that cleaves SNAP23, a non-neuronal SNARE protein.

SNAP23 mediates vesicle-plasma membrane fusion processes, including secretion of airway mucus, antibody, insulin, gastric acids, and ions. The mutated BoNT/E light chain LC/E(K224D) of the present invention showed extended substrate specificity to cleave SNAP23, and the natural substrate, SNAP25, but showed no specificity for, and did not cleave, SNAP29 or SNAP47. Upon direct protein delivery into cultured human epithelial cells, LC/E(K224D) cleaved endogenous SNAP23, which inhibited secretion of mucin and IL-8. These studies show for the first time the feasibility of genetically modifying BoNTs to target a non-neuronal SNARE protein for novel methods of treating human hyper-secretion diseases, such as asthma and chronic obstructive pulmonary disease.

In one embodiment, the present invention is a preparation of an engineered catalytic domain of botulinum neurotoxin E that is capable of specifically cleaving SNAP23. Preferably, the toxin cleaves SNAP25 but not SNAP29 or SNAP 47. The LC/E(K224D) can cleave both SNAP25 and SNAP23, but at ~10 fold lower than Wt-LC/E can cleave SNAP25.

In a preferred embodiment, the modified botulinum neurotoxin E of the present invention has a mutation at light chain residue 224 or a residue corresponding to residue 224. By "residue 224" we mean the lysine at position numbered 224 of SEQ ID NO: 7.SEQ ID NO: 7 is the protein conversion of the DNA sequence of SEQ ED NO: 1 absent the first methionine residue. By "residue corresponding to residue 224" we mean the lysine within the motif of residues 210-240 of SEQ ID NO: 7. Specifically, we mean the highlighted lysine within residues MHELIHSLHGLYGAK-GITTKYTITQKQNPLI (SEQ ID NO: 8). Other botulinum type E subtypes have this same corresponding residue and motif, although the numbering may not be identical among subtypes. However, the motif residues will be at least 90% corresponding to the motif of SEQ ID NO: 8.

One may find an exemplary sequence of botulinum toxin E subtype Beluga light chain at GeneBank with accession number X62089 (SEQ ID NO: 1). We anticipate that other subtypes of serotype E could be used as template for engineering LC that can cleave SNAP23. One would modify residue numbered 224 of any botulinum toxin E subtype in the same manner as disclosed within the present invention.

In a preferred embodiment, the present invention is a preparation of a modified botulinum toxin E with a mutation at a light chain residue 224. Another embodiment of the present invention is a preparation of botulinum neurotoxin E light chain with a mutation at light chain residue 224. Another embodiment of the present invention is a preparation of botulinum neurotoxin catalytic domain (residues 1 through 400) with a mutation at light chain residue 224. Another embodiment of the present invention is a truncated fragment of the catalytic domain, comprising at least residues 1 to 390, which comprises a modified residue 224. By "modified catalytic domain" we mean to include all forms, including humanized forms, of the catalytic domain of L/C BoNT with a modification at residue 224.

Another preferred embodiment is a mutated botulinum neurotoxin E light chain or modified catalytic domain fused to another peptide, as described below, for appropriate therapeutic methods.

In another embodiment, the present invention is a DNA sequence encoding the engineered botulinum neurotoxin or the modified catalytic domain described herein.

An exemplary reference to the sequences of SNAP23, SNAP25, SNAP29 and SNAP47 can be found at GeneBank with accession numbers CR457212 (SEQ ID NO: 2), NM_130811 (SEQ ID NO: 3), CR456582 (SEQ ID NO: 4) and BC011145 (SEQ ID. NO: 5).

In other embodiments of the invention, other mutations of residue 224 would also be suitable. The mutation within LC/E that is being protected is K224D, which recognizes the P2 residue of SNAP23, which is a lysine. We anticipate that a glutamic acid mutation at K224 would also yield a functional LC/E that can cleave SNAP23. We generated a K224A mutation that has the ability to cleave both SNAP23 and SNAP25, but with less efficiency than K224D, which indicates that charge and size of the R-group influence cleavage efficiency. Thus, we anticipate that other residue replacements, such as replacing the lysine at residue 224 of SEQ ID NO: 7 with glutamic acid, may also provide a mutated LC/E with the ability to cleave SNAP23.

In other embodiments, we further anticipate that additional residue replacements, alone or in combination with the mutation of K224D of the present invention, may yield a LC/E that has the ability to cleave SNAP 23 and not SNAP 25.

Methods of Treatment. In other embodiments, the present invention provides novel methods of treating a subject requiring treatment with a botulinum toxin. In one embodiment, the present invention provide methods of treating a subject suffering from a human secretory disease by administering a therapeutically effective amount of the modified catalytic domain as described above.

By "subject" we mean any person requiring treatment with botulinum toxin. By "treating" or "treatment", we mean the management and care of a subject for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder. In one embodiment, we envision the method of the present invention reducing symptoms by at least 20 to 50 percent. We envision treatment occurring on a regular basis until symptoms are reversed. For instance, in one embodiment, treatment would occur daily, weekly or monthly, as needed.

By "therapeutically effective amount" we mean amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors as known to one of skill in the art (40). This method would involve administering to the subject the modified catalytic domain of the engineered botulinum toxin E of the present invention. By "administering" we mean delivering the engineered BoNT of the present invention to the subject. Although the preferable form of the catalytic domain is the botulinum toxin E light chain, the catalytic domain may include forms that are shorter than the light chain,such as the C-terminal truncation mutants of the catalytic domain to residues ~1-390 residues (41), and forms that are larger than the light chain and include the translocation domain or fragments of the translocation domain up to ~residue $F^{1200}$ which includes the N terminus of the HCR domain. In one embodiment, we have engineered a 1-400 which has good solubility and activity.

In one embodiment, the catalytic domain is complexed, either through covalent bonds or attached in some other way, such as cross-linking, to a targeting molecule (targeting system). The targeting molecule is adapted to target the toxin to a cell-surface receptor of interest.

As described above, we envision several forms of the catalytic domain as being effective potential delivery platforms for the K224D mutation. For instance, protein solubility may vary with the application and the chimera that is engineered, therefore different sized catalytic domains may be more useful in specific applications. We anticipate that the amount of effective delivery platform will be similar to the amounts of BoNT used in clinical therapy and that the amount of effective delivery can be fractional based upon the catalytic nature of LC/EK224D.

In other embodiments, a suitable delivery system will, in one embodiment, target specific cell types or cell surface receptors that are internalized and deliver LC/E into the cytoplasm, such as an antibody or a growth factor. Potential cell surface receptors that can be targeted include tissue specific growth factor receptors, which could vary with the disease that is targeted. For example, one of skill would understand based on materials known to the field how to target CD22 in hairy cell leukemia (42).

Alternatively, a lipid-based directed protein delivery system could be used to deliver LC/E directly into the host cytosol. For instance, a targeted-liposome delivery which delivers either the catalytic domain protein directly or DNA encoding the LC/EK224D protein (39) are also effective methods of delivering the engineered BoNT/E of the present invention to treat various diseases. For instance, lipid based delivery system that assemble nano-particles for efficient delivery and reduced immunogenicity should prove useful as targeting vehicles (43). While the different delivery methods may not have different advantages based on the disease being targeted, the specificity of the delivery system will be a critical factor in selecting a specific delivery system.

To optimize the potency, we envision humanizing the modified catalytic domain using one of several possible approaches known to the art (34, 35).

Several delivery systems are envisioned for the therapeutic delivery of LC/E(K224D), or another suitable toxin, to a subject requiring treatment for, for instance, a non-secretory or hyper-secretory disease. Example delivery systems include, withoutlimitation, single chain protein chimeras where the modified catalytic domain, preferably LC/E (K224D), is fused either at the DNA level or by protein-receptor cross-linking (36) or bipartate protein delivery systems where the catalytic domain, preferably LC/E (K224D), is linked to a fusion composed of a di-protein delivery system (37, 38). For example, the gene encoding LC/E(K224D) could be genetically fused to the gene encoding the epidermal growth factor to target non-small-cell lung cancer.

The table below describes some of the appropriate uses for the engineered toxin of the present invention and appropriate targets for the targeting domain.

TABLE 1

| Receptor/Disease | |
|---|---|
| LC/E(K224D)-Receptor | Disease |
| Lung epithelium cell specific receptor | Asthma, CF, chronic obstructive pulmonary disease |
| Gastric specific receptor | Gastric acid efflux and inflammation |
| Mast cell specific receptor | Allergic rhinitis, Hemophagocytic lymphohistiocytosis, and Chronic urticaria |
| Cancer specific receptor | Renal cell carcinoma, Nonsmall cell lung cancer, and gastric cancer, Epithelial ovarian cancer, and Estrogen receptor (ER)-positive breast cancer |

Kits. In an alternate embodiment of the invention, a kit for treating a subject with the modified catalytic domain of the present invention is provided. In one embodiment, the kit comprises a form of the engineered BoNT of the present invention and instructions for use. In one embodiment, the modified catalytic domain of the present invention is formulated, delivered and stored for use in physiologic conditions. In a preferred embodiment, the kit also comprises a targeting system. The modified catalytic domain is either already attached to the targeting system or the kit contains the targeting system with instructions for attachment. In alternate embodiments, the kit comprises DNA encoding LC/E(K224D) that can be used to engineer fusion proteins to specific tissue specific targeting molecules.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

III. Examples

The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

A. Methods and Materials.

Molecular modeling. Molecular modeling was performed using SWISS-MODEL. The structure of the LC/E-SNAP25 (146-202) complex was obtained as described (19), using the crystal structure of LC/E (PDB:3d3x). The structure of LC/E($K^{224}$D)-SNAP23 was modeled using LC/E-SNAP25 complex structure as a template, using PyMol™. Data presented are the average of experiments performed at least 3 times.

Plasmid construction and protein expression. BoNT LC/E expression vector was constructed by amplifying DNA encoding LC/E (1-400) of *Clostridium botulinum* serotype E Beluga (SEQ ID NO: 1) and subcloning into pET-15b. For transfection experiments, LC/E(1-400) was also subcloned into pEGFP vector to generate an EGFP-LC/E (1-400) fusion protein expressed under the CMV promoter. Expression vectors for SNAP23(152-211), SNAP29(202-259) and SNAP47(406-464), the protein equivalents of SNAP25(145-206), were constructed by PCR amplifying and cDNA template: human SNAP23 (ATCC 2900640, SEQ ID NO:2), SNAP29 (ATCC 10700609, SEQ ID NO: 4) and SNAP47 (ATCC 10468826, SEQ ID NO: 5) and subcloning into pGEX-2T. Site-directed mutagenesis was performed using QuickChange (Stratagene). Protein expression and purification were performed as previously described (32).

Cleavage of SNARE protein by LC/E and LC/E($K^{224}D$). Cleavage of SNARE protein was performed as described.

Linear velocity reaction: Reactions contained (10 µl): 5 µM human SNARE proteins, 10 mM Tris-HCl (ph 7.6) with 20 mM NaCl, and the indicated amounts of LC/E and LC/E($K^{224}D$). Reactions were incubated for 10 min at 37° C., subjected to SDS-PAGE and gels were stained with Coomassie. The amount of SNARE protein cleavage was determined by densitometry.

Kinetic parameters: $K_m$ and $k_{cat}$ determinations were made for Wt-LC/E and LC/E derivatives using SNAP25 isoforms. LC concentrations were adjusted to cleave<10% substrate at several concentrations of substrate (1.5~18 µM SNARE protein). Reactions were carried out at 37° C. for 10 min, subjected to SDS-PAGE and the amount of cleaved product was calculated by densitometry. Reaction velocity versus substrate concentration was fit to the Michaelis-Menten equation, using Lineweaver-Burk plots, using SigmaPlot IX (Chicago, Ill.).

LC/E and LC/E($K^{224}D$) activity in human cultured epithelial cells. HeLa cells were cultured in 6 well plates in MEM supplemented with 10% newborn calf serum. Subconfluent cells were transfected with 0.5 or 1.0 µg of indicated plasmid using Lipofectamine LTX (GIBCO/BRL).

Protein delivery. Protein delivery was performed as described (33) with modification. HeLa cells were permeabilized with 1 ml/well of permeabilization buffer containing 30 µM digitonin for 7 min and the incubated in permeabilization buffer with and without the indicated LC.

Protein Secretion Assays: After an overnight incubation, transfected and protein delivered cells were incubated in 2 ml serum free MEM containing 20 ng/ml of TNF-α. After 36 h, 1.5 ml of supernatant was collected, centrifuged at 13,000 g for 1 min, and assayed for secreted mucin and IL-8, using ELISA. Supernatants (150 µl) were mixed with 50 µl of 0.2 M $Na_2CO_3$ (pH 9.6) and added to 96-well plates and incubated overnight at 4° C. Plates were washed and locked with 50 mM $Na_2CO_3$ (pH 9.6) buffer containing 1% (w/v) BSA. Plates were washed and incubated with 100 µl α-mucin IgG (1/200 dilution, Abcam) or α-IL-8 IgG (1/200 dilution, Abcam) for 1 h at RT. Plates were washed 3 and incubated with α-mouse Horse Radish Peroxidase-conjugate antibody (1:10,000 dilution, Pierce) for 1 h at RT. Plates were washed and developed with 100 µl of Ultra-TMB (Pierce) for 20 min at RT and quenched with 100 µl of 1M $H_2SO_4$. $A^{450}$ was expressed as fraction relative to secreted mucin or IL-8 in control supernatants.

Cleavage of SNAP23: lysates from cells incubated with TNF-α for 36 h were assayed for LC/E and LC/E($K^{224}D$)-mediated a cleavage of endogenous SNAP23, using α-SNAP23 mouse IgG (Abcam, Cambridge, Mass.) by Western blot analysis (19).

Delivery Systems. The mutated BoNT was administered to a subject using the following delivery methods:

Target-specific Cell Receptor: One skilled in the art of molecular biology would be able to engineer chimeras of LC/E(K224D) fused to targeting molecules, using polymerase chain reaction-like protocols.

Lipid-based: One skilled in the use of lipid based delivery systems would be able to develop lipid LC/E(K224D) ratios for the efficient internalization of the LC by utilizing a lipid to protein matrix.

Methods of Treatment. The engineered BoNT of the present invention was administered to a subject to treat, in one embodiment, hyper-secretory and non-secretory diseases. One of skill would identify a subject for treatment with the engineered BoNT, administer the treatment, monitor the results, and determine the effectiveness of the treatment, following strategies utilized for the development of immunotoxin therapy in the treatment of hairy cell leukemia.

B. Results.

Previous studies identified residues 167-186 as the minimal, optimal peptide of SNAP25, a 206 amino acid protein for LC/E in vitro cleavage (19). SNAP25 (167-186) comprises two sub-sites that include a substrate binding "B" region and an active site "AS" region (FIG. 1*a*). LC/E recognizes the P3 residue to facilitate alignment of the P2 and P1' residues of SNAP25. The S1' pocket of LC/E is formed by $F^{191}$, $T^{159}$, and $T^{208}$ with hydrophobic interactions between $F^{191}$ of LC/E and the P1' residue $I^{181}$ of SNAP25 (20). The basic S2 pocket contains $K^{224}$, which recognizes the P2 residue $D^{179}$, through a predicted salt bridge. Docking the P2 and P1' residues of SNAP25 into the active site pockets of LC/E aligns the scissile bond for cleavage (19, 20).

BoNT/E was known as not cleaving human SNAP23 (8), providing a framework of defining SNAP isoforms specificity of the BoNTs. Many of the residues that contributed to LC/E recognition of SNAP25 were conserved in human SNAP23, except $T^{173}/A^{179}$, $D^{179}/K^{185}$, $M^{182}/T^{188}$ and $E^{183}/D^{189}$, respectively (FIG. Ib). $T^{173}$ in SNAP25 played only a limited contribution for LC/E substrate recognition (20) and only main chain interactions of M-D contributed to LC/E substrate recognition. Thus, the $T^{173}/A^{179}$, $D^{179}ZK^{185}$, $M^{182}/T^{188}$ and $E^{183}ZD^{189}$ differences between SNAP25 and SNAP23 did not appear to contribute to inability of cle to cleave SNAP23. In contrast, the P2 residue of SNAP25, $D^{179}$, is recognized by the basic S2 pocket of cle via the basic residue, $K^{224}$, which contributes to cle substrate recognition (FIG. Ic, upper panel). Accordingly, the inventors examined whether the sale bridge between $K^{224}$ of LC/E and $D^{179}$ of SNAP25 contributes the ability of cle to cleave SNAP25 and that charge repulsion between $K^{224}$ of cle and the P2 residue of SNAP23, $K^{185}$, contributes to the inability of cle to cleave SNAP23. To test this hypothesis, a point mutation, $K^{224}D$, was introduced into LC/E and tested for the ability to cleave human SNAP23 (FIG. Ic, lower panel).

Figure 2:
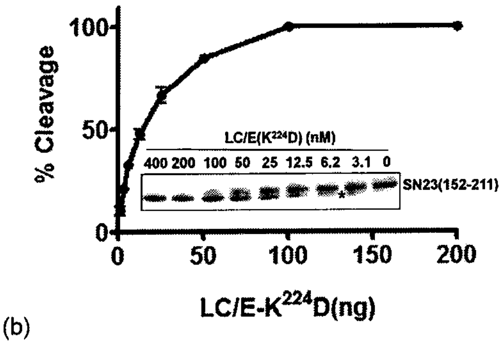
FIG. 2. Cleavage of SNAP23 by LQE($K^{224}$D). (a) Five μm SNAP 23 was incubated with indicated amounts of LC/E($K^{224}$D) and subjected to SDS-PAGE (stained gel is shown in insert, SNAP23(152-211) is designated (SN23 (152-211)) and the cleavage product SNAP23(152-186) is designated*. % SNAP23 cleavage was determined by densitometry, (b) Kinetic constant for LC/E to cleave SNAP25 and LC/E($K^{224}$D) to cleave SNAP23.
Figure 3:
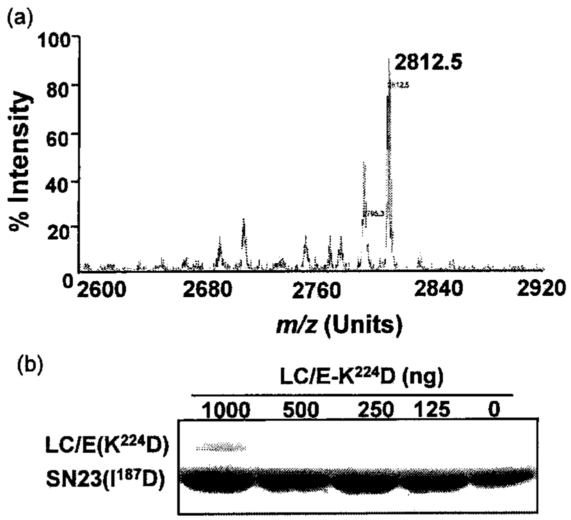
FIG. 3. Site of SNAP23 cleavage by LC/E($K^{224}$D) (a) Five μm SNAP23 was incubated with 2 μm of LC/E($K^{224}$D) and subjected to MALDI-TOF Mass Spectrometry. Intensity (100%) on the y-axis was set to the 2812.5 band and the x-axis represents mass-to-charge units, m/z. (b) SNAP23 ($I^{187}$D) was incubated with the indicated amounts of LC/E ($K^{224}$D) and subjected to SDS-PAGE. The Coomassie stained gel is shown with the migrations of LC/E($K^{224}$D and SNAP23($I^{187}$D) indicated on the left.

LC/E($K^{224}D$) cleaved human SNAP23 with a $K_m$ of ~3 µM and $k_{cat}$ of ~17 $S^{-1}$ (FIG. 2), with 2-fold of the $K_m$ and 5-fold of the $k_{cat}$ of LC/E for the cleavage of human SNAP25. The specific activity for the cleavage of SNAP23 by LC/E($K^{224}D$) was similar to the cleavage of VAMP-2 by the B serotype of BoNT and ~10 fold faster for the cleavage of VAMP-2 by tetanus toxin (21, 22). The site that LC/E ($K^{224}D$) cleaved SNAP23 was identified by MALDI-TOF MS were a major peak with an m/z value of 2812.5 was identified in a reaction mixture that contained SNAP23 and LC/E($K^{224}D$) (FIG. 3*a*), corresponding to the C-terminal 25 amino acid of human SNAP23, IKRITDKADTNRDRIDI-ANARAKKLIDS (SEQ ID NO: 6). This indicated that LC/E($K^{224}D$) cleaved SNAP23 between $^{186}R\text{-}I^{187}$. The determination that LC/E($K^{224}D$) did not cleave SNAP23 ($I^{187}D$) (FIG. 3*b*) supported that LC/E($K^{224}D$) cleaved human SNAP23 between residues $^{186}R\text{-}I^{187}$.

Figure 4:
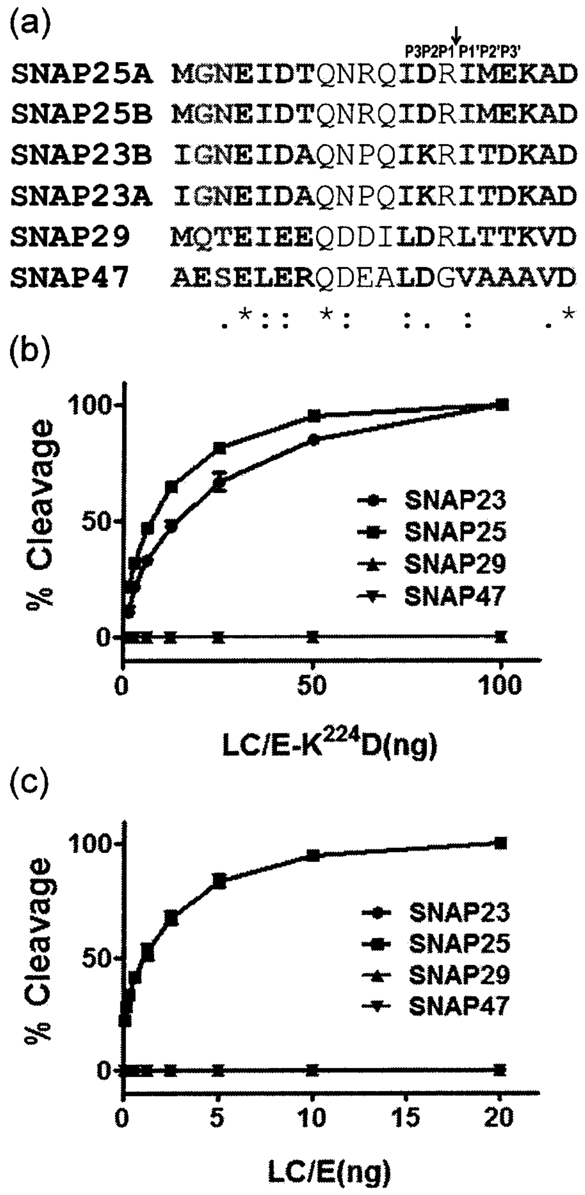
FIG. 4. Sequence alignment and substrate specificity of LC/E($K^{224}$D) and Wt-LC/E on SNAP25 isoforms. (a) Alignment of SNAP23a (SEQ ID NO: 11),SNAP23b (SEQ ID NO: 12), SNAP25a (SEQ ID NO: 13), SNAP25b (SEQ ID NO: 14), SNAP29 (SEQ ID NO: 15) and SNAP47 (ClustalW2) (SEQ ID NO: 16) in the regions corresponding to SNARE proteins that interact with the binding region and active sites region of LC/E. Indicated are conserved residues (*) and similar residues (:, .) among the SNAP25 isoforms. Cleavage site of SNAP25 by LC/E (arrow) and P site resides are indicated. Linear velocity assays of LC/E($K^{224}$D) (b) and Wt-LC/E (c) with the indicated isoforms of SNAP25. Five μm SNAP25 isoform was incubated with the indicated amounts of LC, subjected to SDS-PAGE and gels were stained with Coomassie. The amount of SNAP25 isoform cleavage was determined by densitometry.

SNAP25 isoforms include SNAP25a, SNAP25b, SNAP23a, SNAP23b, SNAP29 and SNAP47 (23, 24). SNAP23 and SNAP25 mediate synaptic membrane fashion in non-neuronal and neuronal cells, respectively, while SNAP29 and SNAP47 have not been implicated in membrane fusion events. SNAP29 was shown to inhibit SNARE disassembly and was implicated in synaptic transmission (25). While the function of SNAP47 is not clear, SNAP47 can substitute for SNAP25 in SNARE complex formation and proteoliposome fashion. The substrate specificity of LC/E($K^{224}$D) on span25 isoforms including SNAP23a, SNAP25b, SNAP29 and SNAP47 were tested. SNAP23b and SNAP25a were not tested because the a-b isoforms of SNAP23 and SNAP25 were identical and the LC/E substrate recognition region (FIG. 4*a*). LC/E($K^{224}$D) showed similar activity on both SNAP23 and SNAP25 (FIG. 4*b*), but did not cleave SNAP29 and SNAP47. Wt-LC/E cleaved SNAP25 (FIG. 4*c*), but not the other SNAP25 isoforms. The specificity of another LC/E $K^{224}$ mutation ($K^{224}$A) on SNAP23 and SNAP25 was also characterized. LC/E($K^{224}$A) cleaved SNAP23 and SNAP25 with similar efficiencies, but at a slower rate than LC/E($K^{224}$D) (data not shown).

Figure 5:
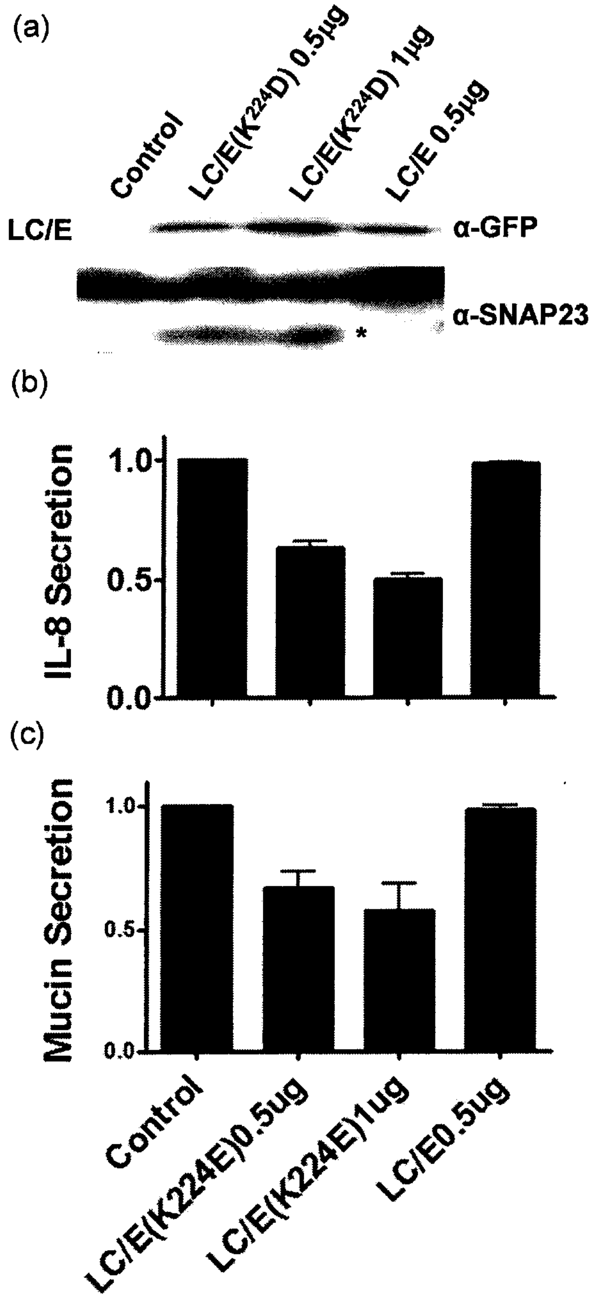
FIG. 5. LC/E($K^{224}$D) cleaves SNAP23 and inhibits mucin and IL-8 secretion in TGF-α stimulated HeLa cells. (A) GFP-LC/E($K^{224}$D) or GFP-Wt-LC/E were transfected into HeLa cells. After 24 h, cell lysates were prepared and separated by SDS-PAGE and cleavage of SNAP23 was measured by western-blotting 3 using anti SNAP-23 mouse monoclonal antibody. (B, C). HeLa cells were transfected with DNA encoding GFP-LC/E($K^{224}$D) or GFP-Wt-LC/E. After 24 h, cells were washed with serum free MEM medium twice and secretion was induced by the addition of serum free MEM medium supplemented with 20 ng/ml of TNF-α. After 36 h, supernatant were collected and assayed for mucin and IL-8 secretion, using an ELISA format. The amount of mucin and IL-8 secreted in controls cells was adjusted to 1.0 and used as a reference for cells treated with TNF-α.

Next, the ability of LC/E($K^{224}$D) to cleave endogenous SNAP23 in HeLa cells was tested. While a role for SNAP23 in constitutive exocytosis is not apparent (26), SNAP23 contributes to regulated exocytosis (27). Transfection of −60% of HeLa cell population with LOE($K^{224}$D) resulted in the cleavage −45% of the SNAP23, while SNAP 23 cleavage was not detected when HeLa cells were transfected with Wt-LC/E or a no plasmid control (FIG. 5). This indicated that LC/E($K^{224}$D), but not Wt-LC/E, cleaved endogenous SNAP23 in cultured cells. The effect of SNAP23 cleavage on HeLa cell secretion was tested in LC/E($K^{224}$D)-transfected HeLa cells by analyzing TNF-α-mediated mucin and IL-8 secretion. Control HeLa cells secreted mucin and IL-8 upon addition of TNF-α, while LC/E($K^{224}$D)-transfected HeLa cells showed reduced mucin and IL-8 secretion (FIG. 5*b* and *c*). The inhibition was specific, since Wt-LC/E-transfected HeLa cells showed the same amount of mucin and IL-8 secretion as control cells and did not cleave endogenous SNAP23 (FIG. 5).

Figure 6:
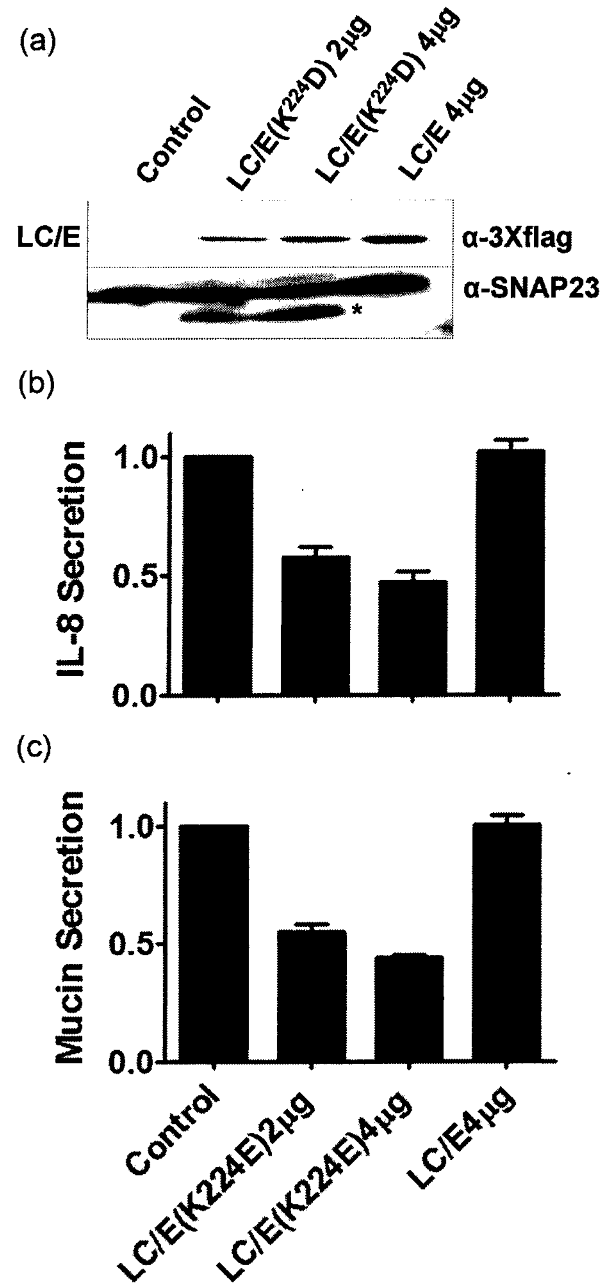
FIG. 6. Recombinant LOE($K^{224}$D) cleaves SNAP23 and inhibits mucin and IL-8 secretion in TGF-α stimulated HeLa cells. HeLa cells were treated with digitonin and then incubated with His-LC/E($K^{224}$D) or His-Wt-LC/E (3-Xflag tagged proteins). After an overnight incubation, cells were washed and then incubated with serum free MEM media supplemented with 20 ng/ml of TNF-α for 36 h when cell supernatants were collected and cell lysates were prepared, (a) Cell lysates were subjected to SDS-PAGE and LC/E expression and SNAP23 cleavage was measured by Western blot, using α-3Xflag antibody and α-SNAP23 antibody, respectively; * indicates migration of the SNAP23 cleavage product. Culture supernatants were assayed IL-8 (b) and mucin (c) secretion, using an ELISA, using 1.0 as a reference for cells treated with recombinant LC/E.

To test the feasibility of utilizing LC/E($K^{224}$D) as a protein therapy, recombinant LC/E($K^{224}$D) was delivered into HeLa cells, using digitonin. Recombinant LC/E($K^{224}$D) cleaved endogenous SNAP23 (FIG. 6), which inhibited TNF-α-mediated mucin and IL-8 secretion (FIGS. 6*b* and *c*). Digitonin treatment also delivered Wt-LC/E into HeLa cells, but Wt-LC/E-treated HeLa cells, did not show detectable inhibition of mucin and IL-8 secretion and did not cleave endogenous SNAP23 (FIG. 6). This supports a role for SNAP23 in regulated exocytosis pathways in epithelial cells and indicates the utility of LC/E($K^{224}$D) as a research tool to study SNAP23-regulated exocytosis (27).

C. Discussion.

Understanding of substrate specificity of botulinum neurotoxins has enabled the engineering of a novel light chain derivative of BoNT/E with extended substrate specificity, providing a proof of principle to extend the clinical potential of BoNT therapy beyond neurological applications. While airway mucus protects the epithelial lining by entrapping and clearing foreign debris, bacteria, and viruses from the airway by ciliary movement, a process termed mucociliary clearance (17, 18), excessive airway mucus secretion, mucus hypersecretion, may cause mucus accumulation that is associated with human clinical conditions such as asthma and chronic obstructive pulmonary disease where mucus accumulation contributes to respiratory diseases. Mucus secretion is a regulated process coordinated by several molecules, including SNARE proteins, myristoylated alanine-rich C kinase substrate (MARCKS), and Munc proteins, which coordinate the docking of mucin containing vesicles with the secretory cell plasma membrane for exocytosis (17, 18). Targeting SNAP23 by a substrate modified BoNT may reduce the secretion processes of hypersecretion syndromes. A SNAP23-specific BoNT may also be targeted for other therapeutic applications that include diabetes and inflammatory and immune disorders which also include a hypersecretory component (28, 29).

Alignment and biochemical analyses allow prediction of the mechanism for the catalytic activity of Wt-LC/E and LC/E(K224D) on SNAP25 isoforms. The low overall homology within the active site regions of SNAP29 and SNAP47 to SNAP25 and the lack of an isoleucine at the P1' site explain the inability of Wt-LC/E and LC/E(K224D) to cleave SNAP29 and SNAP47. In contrast, the overall homology between SNAP23 and SNAP25 is high, except at the P2, P2' and P3' residues with the most dramatic change at the P2 residue where SNAP25 contains an aspartate and SNAP23 contains a lysine. Thus, one reason for the inability of Wt-LC/E to cleave SNAP23 may be due to the electrostatic repulsion of the P2 residue lysine within SNAP23 by $K^{224}$ of LC/E. This may destabilize the S2 pocket and affect alignment of the P1' residue into the S1' pocket. The ability of LC/E(K224D) to cleave SNAP23 may be due to the introduction of a salt bridge between the P2 residue Lys of SNAP23 and the mutated S2 pocket residue $D^{224}$. LC/E (K224D) also retained the ability to cleave SNAP25, although at a rate that was ~10 fold slower than Wt-LC/E. This suggests that the repulsion between the P2 residue aspartate of SNAP25 and the mutated S2 pocket residue $D^{224}$ was not sufficient to inhibit sessile bond cleavage by LC/E($K^{224}$D).

Since LC/E(K224A) cleaved SNAP25 and SNAP23, but at a reduced rate relative to LC/K224D, both charge and size of the R-group at residue 224 contribute to optimal scissile bond cleavage. Overall, the biochemical properties of LC/E and LC/E-$K^{224}$ derivatives are consistent with P2 residue-S2 pocket residue interactions contributing to the efficiency of sessile bond cleavage. While the to bind SNAP29 and SNAP47. In contrast, the overall homology between SNAP23 and SNAP25 is high, except at the P2, P2' and P3' residues with the most dramatic change at the P2 residue where SNAP25 contains an aspartate and SNAP23 contains a lysine. Thus, one reason for the inability of Wt-LC/E to cleave SNAP23 may be due to electrostatic repulsion of the P2 residue lysine within SNAP23 by $K^{224}$ of LC/E. This may destabilize the S2 pocket and affect alignment of the PI' residue into the S1' pocket.

The ability of LC/E(K224D) to cleave SNAP23 may be due to the introduction a salt bridge between the P2 residue Lys ofSNAP23 and the mutated S2 pocket residue $D^{224}$. LC/E(K224D) also retained the ability to cleave SNAP25, although at a rate that was −10 fold slower than Wt-LC/E. This suggests that the repulsion between the P2 residue aspartate of SNAP25 and the mutated S2 pocket residue $D^{224}$ was not sufficient to inhibit sessile bond cleavage by LOE($K^{224}$D). Since LC/E($K^{224}$A) cleaved SNAP25 and-SNAP23, but at a reduced rate relative to LC/E$K^{224}$D, both charge and size of the R-group at residue 224 contribute to optimal scissile bond cleavage. Overall, the biochemical properties of LC/E and LC/E-$K^{224}$ derivatives are consistent with P2 residue-S2 pocket residue interactions contributing to the efficiency of sessile bond cleavage. While the ability of native LC/E to bind SNAP23 has not been determined, kinetic values for LC/E and SNAP25 and LC/E($K^{224}$D) and SNAP23 are within 2-fold, indicating similar binding affinities.

Alignment of SNAP25 and SNAP23 within the LC/E binding region (FIG. 1) is nearly identical with 7 of 8 residues identical and the non-identical pair being T:A; a conserved substitution pair, which also supports similar binding affinities of LC/E for SNAP25 and SNAP23. SNARE proteins are key proteins in membrane fusion and trafficking within neuronal secretary pathways (9). The use of BoNT has contributed to the understanding vesicle fusion and neurotransmitter release mechanisms in neuronal cells. The ability of a BoNT derivative to cleave non-neurological SNAREs may provide a useful tool to investigate intracellular vesicular trafficking and the mechanism of membrane fusion in normeuronal systems.

Although BoNT/A could be considered the logical serotype to be engineered for novel applications due to its wide clinical applications, analysis of the mechanisms of SNAP25 recognition indicate that LC/A requires a longer substrate for optimal SNAP25 recognition with a greater number of residue interactions than LC/E (20). The less-complex SNAP25-LC/E interactions make BoNT/E amenable for engineering to modify substrate recognition. In addition, alignment of human SNAP25 and SNAP23 showed that these proteins had a high level of homology at the P3 and PI' sites that are involved in SNAP25 recognition by LC/E. Thus, BoNT/E is a useful platform to engineer mutations that effect SNARE protein recognition. The successful delivery of LC/E($K^{224}$D) into cells to inhibit IL-8 and mucin secretion supports a role for LC/E($K^{224}$D) as a research tool and also shows the potential for therapy to regulate human hypersecretion diseases such as asthma and inflammatory diseases. The therapeutic specificity of LC/E$K^{224}$D would be based upon the receptor binding component, as described for toxin chimeras, such as diphtheria toxin A fragment-IL2 (30) and Exotoxin A fragment-IgG variable region fragment (31). In conclusion, the current study shows proof of principle for altered substrate specificity to extend the application of BoNTs beyond neurological inflictions.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Montecucco C & Schiavo G (1994) Mechanism of action of tetanus and botulinum neurotoxins. Mol Microbiol 13(1):1-8.
2. Poulain B & Humeau Y (2003) Mode of action of botulinum neurotoxin: pathological, cellular and molecular aspect. Ann Readapt Med Phys 46(6):265-275.
3. Dong M, et al. (2003) Synaptotagmins I and II mediate entry of botulinum neurotoxin B into cells. Cell Biol 162(7):1293-1303.
4. Dong M, et al. (2006) SV2 is the protein receptor for botulinum neurotoxin A. Science 312(5773):592-596.
5. Rummel A, Karnath T, Henke T, Bigalke H, & Binz T (2004) Synaptotagmins I and II act as nerve cell receptors for botulinum neurotoxin G. J Biol Chem 279(29):30865-30870.
6. Brunger A T (2005) Structure and function of SNARE and SNARE-interacting proteins. Q Rev Biophys 38(1):1-47.
7. Sadoul K, et al. (1997) SNAP-23 is not cleaved by botulinum neurotoxin E and can replace SNAP-25 in the process of insulin secretion. J Biol Chem 272(52):33023-33027.
8. Vaidyanathan V V, et al. (1999) Proteolysis of SNAP-25 isoforms by botulinum neurotoxin types A, C, and E: domains and amino acid residues controlling the formation of enzyme-substrate complexes and cleavage. J Neurochem 72(1):327-337.
9. Jahn R & Scheller R H (2006) SNAREs—engines for membrane fusion. Nat Rev Mol Cell Biol 7(9):631-643.
10. Mahajan S T & Brubaker L (2006) Botulinum toxin: From life-threatening disease to novel medical therapy. Am J Obstet Gynecol.
11. Mahajan S T & Brubaker L (2007) Botulinum toxin: from life-threatening disease to novel medical therapy. Am J Obstet GynecoI 196(1):7-15.
12. Glogau R G (2002) Review of the use of botulinum toxin for hyperhidrosis and cosmetic purposes. Clin J Pain 18(6 Suppl):SI91-197.
13. Cheng C M, Chen J S, & Patel R P (2006) Unlabeled uses of botulinum toxins: a review, part 2. Am J Health Syst Pharm 63(3):225-232.
14. Chaddock J A, et al. (2004) Retargeted clostridial endopeptidases: inhibition of nociceptive neurotransmitter release in vitro, and antinociceptive activity in in vivo models of pain. Mov Disord 19 Supp 18:S42-47.
15. Duggan MJ, et al. (2002) Inhibition of release of neurotransmitters from rat dorsal root ganglia by a novel conjugate of a *Clostridium botulinum* toxin A endopeptidase fragment and Erythrina cristagalli lectin. J Biol Chem 277(38):34846-134852.
16. Foster K A, et al. (2006) Re-engineering the target specificity of Clostridial neurotoxins—a route to novel therapeutics. Neurotox Res 9(2-3): 101-107.
17. Davis C W & Dickey B F (2008) Regulated airway goblet cell mucin secretion. Annu Rev Physiol 70:487-512.
18. Rogers D F (2007) Physiology of airway mucus secretion and pathophysiology of hypersecretion. Respir Care 52(9):1134-1146; discussion 1146-1139.
19. Chen S & Barbieri J T (2007) Multiple pocket recognition of SNAP25 by botulinum neurotoxin serotype E. J Biol Chem 282(35):25540-25547.
20. Chen S & Barbieri J T (2006) Unique substrate recognition by botulinum neurotoxins serotypes A and E. J Biol Chem 281 (16): 10906-10911.
21. Sikorra S, Henke T, Galli T, & Binz T (2008) Substrate recognition mechanism of V AMP/synaptobrevin-cleaving clostridial neurotoxins. J Biol Chem 283(30):21145-21152.
22. Chen S, Hall C, & Barbieri J T (2008) Substrate recognition of VAMP-2 by botulinum neurotoxin B and tetanus neurotoxin. J Biol Chem 283(30):21153-21159.

23. Oyler G A, et al. (1989) The identification of a novel synaptosomal-associated protein, SNAP-25, differentially expressed by neuronal subpopulations. J Cell Biol 109(6 Pt 1):3039-3052.
24. Holt M, et al. (2006) Identification of SNAP-47, a novel Qbc-SNARE with ubiquitous expression. J Biol Chem 281(25):17076-17083.
25. Pan P Y, et al. (2005) SNAP-29-mediated modulation of synaptic transmission in cultured hippocampal neurons. J Biol Chem 280(27):25769-25779.
26. Okayama M, Arakawa T, Mizoguchi I, Tajima Y, & Takuma T (2007) SNAP-23 is not essential for constitutive exocytosis in HeLa cells. FEBS Lett 581(24):4583-4588.
27. Abonyo B O, et al. (2004) Syntaxin 2 and SNAP-23 are required for regulated surfactant secretion. Biochemistry 43(12):3499-3506.
28. Martin-Martin B, Nabokina S M, Blasi J, Lazo P A, & Mollinedo F (2000) Involvement of SNAP-23 and syntaxin 6 in human neutrophil exocytosis. Blood 96(7): 2574-2583.
29. Pagan J K, et al. (2003) The t-SNARE syntaxin 4 is regulated during macrophage activation to function in membrane traffic and cytokine secretion. Curr Biol 13(2): 156-160.
30. Strom TB, et al. (1991) Immunotoxins and cytokine toxin fusion proteins. Ann N Y Acad Sci 636:233-250.
31. Du X, Ho M, & Pastan I (2007) New immunotoxins targeting CD123, a stem cell antigen on acute myeloid leukemia cells. J Immunother 30(6):607-613.
32. Baldwin M R & Barbieri J T (2007) Association of botulinum neurotoxin serotypes A and B with synaptic vesicle protein complexes. Biochemistry 46(11):3200-3210.
33. Washbourne P, et al. (2001) Cysteine residues of SNAP-25 are required for SNARE disassembly and exocytosis, but not for membrane targeting. Biochem J 357(Pt 3):625-634.
34. Winter, G. Harris, W. J. Humanized antibodies 1993, 14:6:243-6.
35. Nishibori, N. Horiuchi, H. Furusawa, S. Matsuda, H. Humanization of chicken monoclonal antibody using phage-display system. 2006, Mol Immunol, 43:6: 634-42.
36. Strom T B, et al. (1991) Immunotoxins and cytokine toxin fusion proteins. Ann N Y Acad Sci 636:233-250.
37. Du X, Ho M, & Pastan I (2007) New immunotoxins targeting CD123, a stem cell antigen on acute myeloid leukemia cells. J Immunother 30(6):607-613.
38. Milne J C, Blanke S R, Hanna P C, Collier R J. (1995) Protective antigen-binding domain of anthrax lethal factor mediates translocation of a heterologous protein fused to its amino- or carboxy-terminus. Molecular Microbiology 15(4):661-6.
39. Haynes S M, Longmuir K J, Robertson R T, Baratta J L, Waring A J. Drug Deliv. (2008) 15(4):207-17.
40. Neurology. 2008 May 6; 70(19):1699-706. Assessment: Botulinum neurotoxin for the treatment of movement disorders (an evidence-based review): report of the Therapeutics and Technology Assessment Subcommittee of the American Academy of Neurology.
41. Proc Natl Acad Sci USA. 2009 106(23):9180-4. Engineering botulinum neurotoxin to extend therapeutic intervention. Barbeiri et al.
42. J Clin Oncol. 2009, 27(18):2983-90. Phase II trial of recombinant immunotoxin RFB4(dsFv)-PE38 (BL22) in patients with hairy cell leukemia.
43. Int J Pharm. 2000 Apr. 25; 200(1):27-39. Novel therapeutic nano-particles (lipocores): trapping poorly water soluble compounds.

We claim:

1. A polypeptide comprising amino acid residues 1-400 of SEQ ID NO:7, wherein the lysine residue at position 224 of SEQ ID NO:7 is substituted by an amino acid residue other than a lysine residue.

2. The polypeptide of claim 1, wherein the lysine residue at position 224 of SEQ ID NO: 7 has been altered to be aspartic acid, glutamic acid, or alanine.

3. The polypeptide of claim 1, wherein the lysine residue at position 224 of SEQ ID NO: 7 has been altered to be aspartic acid.

* * * * *

SEQUENCE LISTING

```
<160> NUMBER OF SEQ ID NOS: 16

<210> SEQ ID NO 1
<211> LENGTH: 4017
<212> TYPE: DNA
<213> ORGANISM: Clostridium botulinum

<400> SEQUENCE: 1

gaattcaagt agtagataat aaaaataatg ccacagattt ttattattaa taatgatata      60

tttatctcta actgtttaac tttaacttat aacaatgtaa atatatattt gtctataaaa     120

aatcaagatt acaattgggt tatatgtgat cttaatcatg atataccaaa aaagtcatat     180

ctatggatat taaaaaatat ataaatttaa aattaggaga tgctgtatat gccaaaaatt     240

aatagtttta attataatga tcctgttaat gatagaacaa ttttatatat taaaccaggc     300

ggttgtcaag aattttataa atcatttaat attatgaaaa atatttggat aattccagag     360

agaaatgtaa ttggtacaac cccccaagat tttcatccgc ctacttcatt aaaaaatgga     420

gatagtagtt attatgaccc taattattta caaagtgatg aagaaaagga tagattttta     480

aaaatagtca caaaaatatt taatagaata aataataatc tttcaggagg gattttatta     540

gaagaactgt caaaagctaa tccatattta gggaatgata atactccaga taatcaattc     600

catattggtg atgcatcagc agttgagatt aaattctcaa atggtagcca agacatacta     660

ttacctaatg ttattataat gggagcagag cctgatttat ttgaaactaa cagttccaat     720

atttctctaa gaaataatta tatgccaagc aatcaccgtt ttggatcaat agctatagta     780
```

-continued

```
acattctcac ctgaatattc ttttagattt aatgataatt gtatgaatga atttattcaa    840
gatcctgctc ttacattaat gcatgaatta atacattcat tacatggact atatggggct    900
aaagggatta ctacaaagta tactataaca caaaaacaaa atcccctaat aacaaatata    960
agaggtacaa atattgaaga attcttaact tttggaggta ctgatttaaa cattattact   1020
agtgctcagt ccaatgatat ctatactaat cttctagctg attataaaaa aatagcgtct   1080
aaacttagca aagtacaagt atctaatcca ctacttaatc cttataaaga tgtttttgaa   1140
gcaaagtatg gattagataa agatgctagc ggaatttatt cggtaaatat aaacaaattt   1200
aatgatattt ttaaaaaatt atacagcttt acggaatttg atttacgaac taaatttcaa   1260
gttaaatgta ggcaaactta tattggacag tataaatact tcaaactttc aaacttgtta   1320
aatgattcta tttataatat atcagaaggc tataatataa ataatttaaa ggtaaatttt   1380
agaggacaga atgcaaattt aaatcctaga attattacac caattacagg tagaggacta   1440
gtaaaaaaaa tcattagatt ttgtaaaaat attgtttctg taaaaggcat aaggaaatca   1500
atatgtatcg aaataaataa tggtgagtta ttttttgtgg cttccgagaa tagttataat   1560
gatgataata taaatactcc taaagaaatt gacgatacag taacttcaaa taataattat   1620
gaaaatgatt tagatcaggt tattttaaat tttaatagtg aatcagcacc tggactttca   1680
gatgaaaaat taaatttaac tatccaaaat gatgcttata taccaaaata tgattctaat   1740
ggaacaagtg atatagaaca acatgatgtt aatgaactta atgtattttt ctatttagat   1800
gcacagaaag tgcccgaagg tgaaaataat gtcaatctca cctcttcaat tgatacagca   1860
ttattagaac aacctaaaat atatacattt ttttcatcag aatttattaa taatgtcaat   1920
aaacctgtgc aagcagcatt atttgtaagc tggatacaac aagtgttagt agattttact   1980
actgaagcta accaaaaaag tactgttgat aaaattgcag atatttctat agttgttcca   2040
tatataggtc ttgctttaaa tataggaaat gaagcacaaa aaggaaattt taaagatgca   2100
cttgaattat taggagcagg tattttatta gaatttgaac ccgagctttt aattcctaca   2160
attttagtat tcacgataaa atcttttta ggttcatctg ataataaaaa taaagttatt   2220
aaagcaataa ataatgcatt gaaagaaaga gatgaaaaat ggaaagaagt atatagtttt   2280
atagtatcga attggatgac taaaattaat acacaattta ataaaagaaa agaacaaatg   2340
tatcaagctt tacaaaatca agtaaatgca attaaaacaa taatagaatc taagtataat   2400
agttatactt tagaggaaaa aaatgagctt acaaataaat atgatattaa gcaaatagaa   2460
aatgaactta atcaaaaggt ttctatagca atgaataata tagacaggtt cttaactgaa   2520
agttctatat cctatttaat gaaaataata aatgaagtaa aaattaataa attaagagaa   2580
tatgatgaga atgtcaaaac gtatttattg aattatatta tacaacatgg atcaatcttg   2640
ggagagagtc agcaagaact aaattctatg gtaactgata ccctaaataa tagtattcct   2700
tttaagcttt cttcttatac agatgataaa attttaattt catattttaa taaattcttt   2760
aagagaatta aaagtagttc agttttaaat atgagatata aaaatgataa atacgtagat   2820
acttcaggat atgattcaaa tataaatatt aatggagatg tatataaata tccaactaat   2880
aaaaatcaat ttggaatata taatgataaa cttagtgaag ttaatatatc tcaaaatgat   2940
tacattatat atgataataa atataaaaat tttagtatta gtttttgggt aagaattcct   3000
aactatgata ataagatagt aaatgttaat aatgaataca ctataataaa ttgtatgaga   3060
gataataatt caggatggaa agtatctctt aatcataatg aaataatttg gacattcgaa   3120
gataatcgag gaattaatca aaaattagca tttaactatg gtaacgcaaa tggtatttct   3180
```

gattatataa ataagtggat ttttgtaact ataactaatg atagattagg agattctaaa 3240
ctttatatta atggaaattt aatagatcaa aaatcaattt taaatttagg taatattcat 3300
gttagtgaca atatattatt taaaatagtt aattgtagtt atacaagata tattggtatt 3360
agatatttta atatttttga taaagaatta gatgaaacag aaattcaaac tttatatagc 3420
aatgaaccta atacaaatat tttgaaggat ttttggggaa attatttgct ttatgacaaa 3480
gaatactatt tattaaatgt gttaaaacca aataacttta ttgataggag aaaagattct 3540
actttaagca ttaataatat aagaagcact attcttttag ctaatagatt atatagtgga 3600
ataaaagtta aaatacaaag agttaataat agtagtacta acgataatct tgttagaaag 3660
aatgatcagg tatatattaa ttttgtagcc agcaaaactc acttatttcc attatatgct 3720
gatacagcta ccacaaataa agagaaaaca ataaaaatat catcatctgg caatagattt 3780
aatcaagtag tagttatgaa ttcagtagga aattgtacaa tgaattttaa aaataataat 3840
ggaaataata ttgggttgtt aggtttcaag gcagatactg tcgttgctag tacttggtat 3900
tatacacata tgagagatca tacaaacagc aatggatgtt tttggaactt tatttctgaa 3960
gaacatggat ggcaagaaaa ataaaaatta gattaaacgg ctaaagtcat aaattcc 4017

<210> SEQ ID NO 2
<211> LENGTH: 636
<212> TYPE: DNA
<213> ORGANISM: Homo sapiens

<400> SEQUENCE: 2
atggataatc tgtcatcaga agaaattcaa cagagagctc accagattac tgatgagtct 60
ctggaaagta cgaggagaat cctgggttta gccattgagt ctcaggatgc aggaatcaag 120
accatcacta tgctggatga acaaaaggaa caactaaacc gcatagaaga aggcttggac 180
caaataaata aggacatgag agagacagag aagactttaa cagaactcaa caaatgctgt 240
ggcctttgtg tctgcccatg taatagaaca aagaactttg agtctggcaa ggcttataag 300
acaacatggg gagatggtgg agaaaactca ccttgcaatg tagtatctaa acagccaggc 360
ccggtgacaa atggtcagct tcagcaacca acaacaggag cagccagtgg tggatacatt 420
aaacgcataa ctaatgatgc cagagaagat gaaatggaag agaacctgac tcaagtgggc 480
agtatcctgg gaaatctaaa agacatggcc ctgaacatag gcaatgagat tgatgctcaa 540
aatccacaaa taaaacgaat cacagacaag gctgacacca acagagatcg tattgatatt 600
gccaatgcca gagcaaagaa actcattgac agttaa 636

<210> SEQ ID NO 3
<211> LENGTH: 2053
<212> TYPE: DNA
<213> ORGANISM: Homo sapiens

<400> SEQUENCE: 3
catctttgat gagggcagag ctcacgttgc attgaagacg aaacctcggg gaggtcaggc 60
gctgtctttc cttccctccc tgctcggcgg ctccaccaca gttgcaacct gcagaggccc 120
ggagaacaca accctcccga gaagcccagg tccagagcca aacccgtcac tgacccccca 180
gcccaggcgc ccagccactc cccaccgcta ccatggccga agacgcagac atgcgcaatg 240
agctggagga gatgcagcga agggctgacc agttggctga tgagtcgctg gaaagcaccc 300
gtcgtatgct gcaactggtt gaagagagta aagatgctgg tatcaggact ttggttatgt 360
tggatgaaca aggagaacaa ctggaacgca ttgaggaagg gatggaccaa atcaataagg 420

-continued

```
acatgaaaga agcagaaaag aatttgacgg acctaggaaa attctgcggg ctttgtgtgt    480

gtccctgtaa caagcttaaa tcaagtgatg cttacaaaaa agcctggggc aataatcagg    540

acggagtggt ggccagccag cctgctcgtg tagtggacga acgggagcag atggccatca    600

gtggcggctt catccgcagg gtaacaaatg atgcccgaga aaatgaaatg gatgaaaacc    660

tagagcaggt gagcggcatc atcgggaacc tccgtcacat ggccctggat atgggcaatg    720

agatcgatac acagaatcgc cagatcgaca ggatcatgga gaaggctgat tccaacaaaa    780

ccagaattga tgaggccaac caacgtgcaa caaagatgct gggaagtggt taagtgtgcc    840

cacccgtgtt ctcctccaaa tgctgtcggg caagatagct ccttcatgct tttctcatgg    900

tattatctag taggtctgca cacataacac acatcagtcc acccccattg tgaatgttgt    960

cctgtgtcat ctgtcagctt cccaacaata ctttgtgtct tttgttctct cttggtctct   1020

ttctttccaa aggttgtaca tagtggtcat ttggtggctc taactccttg atgtcttgag   1080

tttcattttt cattttctct cctcggtggc atttgctgaa taacaacaat ttaggaatgc   1140

tcaatgtgct gttgattctt tcaatccaca gtattgttct tgtaaaactg tgacattcca   1200

cagagttact gccacggtcc tttgagtgtc aggctctgaa tctctcaaaa tgtgccgtct   1260

ttggttcctc atggctgtta tctgtcttta tgatttcatg attagacaat gtggaattac   1320

ataacaggca ttgcactaaa agtgatgtga tttatgcatt tatgcatgag aactaaatag   1380

atttttagat tcctacttaa acaaaaactt tccatgacag tagcatactg atgagacaac   1440

acacacacac acaaaacaac agcaacaaca acagaacaac aacaaagcat gctcagtatt   1500

gagacactgt caagattaag ttataccagc aaaagtgcag tagtgtcact tttttcctgt   1560

caatatatag agacttctaa atcataatca tcctttttta aaaaaaagaa ttttaaaaaa   1620

gatggatttg acacactcac catttaatca tttccagcaa aatatatgtt tggctgaaat   1680

tatgtcaaat ggatgtaata tagggtttgt ttgctgcttt tgatggctac gttttggaga   1740

gagcaatctt gctgtgaaac agtgtggatg taaattttat aaggctgact cttactaacc   1800

accatttccc ctgtggtttg ttatcagtac aattctttgt tgcttaatct agagctatgc   1860

acaccaaatt gctgagatgt ttagtagctg ataaagaaac cttttaaaaa aataatataa   1920

atgaatgaaa tataaactgt gagataaata tcattatagc atgtaatatt aaattcctcc   1980

tgtctcctct gtcagtttgt gaagtgattg acattttgta gctagtttaa aattattaaa   2040

aattatagac tcc                                                        2053


<210> SEQ ID NO 4
<211> LENGTH: 1019
<212> TYPE: DNA
<213> ORGANISM: Homo sapiens

<400> SEQUENCE: 4

tctgtttccc agaccgagag ccgcgccggc accatgtcag cttaccctaa aagctacaat     60

ccgttcgacg acgacgggga ggacgaaggc gcccggccgg cccccttggag ggacgcccga   120

gacctccccg acgggcccga cgcgcccgcg gacaggcagc agtacttgcg gcaggaggtc    180

ctccgcaggg ctgaggccac ggccgccagc accagcaggt ccctggccct catgtacgag    240

tccgagaagg ttggggtcgc ctcttccgag gagctcgccc gtcagcgagg agtcctggag    300

cgcacagaga agatggtgga caagatggac caagatttga agatcagcca gaaacacatc    360

aatagcatta agagcgtgtt tggggggctg gtcaattact tcaaatccaa accagtagag    420

accccacctg aacagaatgg caccctcacc tcccagccca acaacagatt gaaagaagct    480
```

-continued ataagtacaa gtaaagaaca ggaagcaaag taccaggcca gccacccaaa ccttagaaag 540
ctggatgata cagaccctgt ccccagaggg gctggttctg ccatgagtac tgatgcttac 600
ccaaagaacc cacaccttcg agcctatcac cagaagatcg acagcaacct agatgagctg 660
tccatgggac tgggtcgtct gaaggacata gccctgggga tgcagacaga aattgaggag 720
caagatgaca ttcttgaccg gctgacaacc aaagtggaca agttagatgt caacataaaa 780
agcacagaaa gaaaagttcg acaactctga agacagacgg atttccactc tattgtgatg 840
aaaagatttg aaagatcttt ttttgaactt ccaagaaatt tcatttacta ttttagtatg 900
taaattaatg tgtgtttgca aatgttataa tagagtaggt cttaagacat tttgctgtt 960 ataaggaagt gtttgtccca cattttccta gggttaacac ctcaccaagt tcttccagc 1019

<210> SEQ ID NO 5
<211> LENGTH: 1925
<212> TYPE: DNA
<213> ORGANISM: Homo sapiens

<400> SEQUENCE: 5
ggcgccgagc ggccgaggcg ccgcggtcgg ctctgggact cgtctggcgt ccctcagagg 60
cagaagaggc ctggaccttg gcgcacacag acccaggaac agatgagcag ggatgtctgc 120
atccacacct ggccgtgcac ctactacctg gagcccaaga ggcgatgggt tactggacag 180
ctgtccttaa catcgctgtc gctcaggttc atgactgaca gcactggaga gattctggtc 240
agcttccccc tctccagcat agttgagatc aagaaggagg cttcacattt tatcttcagc 300
tccatcacca tcctggagaa gcgccatgcc aagcactggt tcagctccct gcggccaagt 360
cgaaatgtgg tcttcagcat catcgagcat ttctggaggg agctgctgct gtctcagcct 420
ggagccgtgg cagacgcatc tgtcccaagg acccggggcg aggagctgac gggactcatg 480
gctggatccc agaaacgcct ggaggacacg gcgagggtcc tgcaccacca gggccagcag 540
ctggacagcg tcatgagagg cctggacaag atggagtcag acctggaggt ggcggacaga 600
ttgctgacag aactggaatc tcctgcttgg tggcccttta gctccaagct ttggaagaca 660
ccaccggaaa caaagcccag ggaagatgtc tccatgacca gttgtgaacc ctttgggaaa 720
gaagggatac tgataaaaat tcctgctgtt atttcccaca gaacagagtc tcacgttaaa 780
ccagggaggc tcaccgtcct tgtgtctggg ttggaaatac atgactccag ttctttgctc 840
atgcacaggt ttgaaagaga agacgtggac gacatcaagg tccactcacc ttacgaaatt 900
agcatccgcc agcggtttat tggaaagcca gacatggcct atcgtttgat atctgccaag 960
atgccagagg ttatccccat tttagaagtg cagttcagca agaagatgga gctgttagaa 1020
gatgcattgg tgctcagaag cgcaagaacc tcttccccccg cagagaagag ctgctcagtc 1080
tggcatgcag catctgggct gatgggccgt accctgcacc gtgagccacc cgcaggagac 1140
caggagggca cagcactgca cctgcagaca agcctgccag ccctttctga ggcagatacc 1200
caggaactaa cccagatcct gaggaggatg aaggggctgg ccctggaggc cgagagtgag 1260
ctggagagac aagacgaagc cctggatggc gttgcagcag ctgtggacag ggcaaccttg 1320
accatcgaca agcacaacag gcggatgaag aggctgacct aggggcagaa cgtccctgca 1380
ttcctgtctc accctgcaca tcccgctgag atggagggct gggcggcagt gccagggctg 1440
cagaggcctg tggccctccg gagtggtctt cctctggatg ggctgctac tgtggggctg 1500 cttctgcacc aggggcctcc ccaggtgtgc accatgcctg cctcccactt ggctgtccct 1560
gctgctgggc aggacccggc cacatgttct gcggatgctg cagaagtgtg gaccatggcg 1620

-continued ggaccccaag gacacttggc acaggcctgg aagaggccgc cctcgtcttg tctcggctcc 1680
ctttcatgga cagactggcc ttcttagctg tactataaat ttgtgagtga agttagagcc 1740
cagctcactt agccagctca ctttgagggc atcctataaa cacccaactg ttcttttatc 1800
gtctcggttt tagccaaaag tgaaattagc atgactgcat ctttcaaaca aaaatattga 1860
tttctgcttt tagggccccg tttccatcca gaaataaagg gaaatgctgg aaaaaaaaaa 1920
aaaaa 1925

<210> SEQ ID NO 6
<211> LENGTH: 28
<212> TYPE: PRT
<213> ORGANISM: Homo sapiens

<400> SEQUENCE: 6

Ile Lys Arg Ile Thr Asp Lys Ala Asp Thr Asn Arg Asp Arg Ile Asp
1 5 10 15

Ile Ala Asn Ala Arg Ala Lys Lys Leu Ile Asp Ser
20 25

<210> SEQ ID NO 7
<211> LENGTH: 1250
<212> TYPE: PRT
<213> ORGANISM: Clostridium botulinum

<400> SEQUENCE: 7

Pro Lys Ile Asn Ser Phe Asn Tyr Asn Asp Pro Val Asn Asp Arg Thr
1 5 10 15

Ile Leu Tyr Ile Lys Pro Gly Gly Cys Gln Glu Phe Tyr Lys Ser Phe
20 25 30

Asn Ile Met Lys Asn Ile Trp Ile Ile Pro Glu Arg Asn Val Ile Gly
35 40 45

Thr Thr Pro Gln Asp Phe His Pro Pro Thr Ser Leu Lys Asn Gly Asp
50 55 60

Ser Ser Tyr Tyr Asp Pro Asn Tyr Leu Gln Ser Asp Glu Glu Lys Asp
65 70 75 80

Arg Phe Leu Lys Ile Val Thr Lys Ile Phe Asn Arg Ile Asn Asn Asn
85 90 95

Leu Ser Gly Gly Ile Leu Leu Glu Glu Leu Ser Lys Ala Asn Pro Tyr
100 105 110

Leu Gly Asn Asp Asn Thr Pro Asp Asn Gln Phe His Ile Gly Asp Ala
115 120 125

Ser Ala Val Glu Ile Lys Phe Ser Asn Gly Ser Gln Asp Ile Leu Leu
130 135 140

Pro Asn Val Ile Ile Met Gly Ala Glu Pro Asp Leu Phe Glu Thr Asn
145 150 155 160

Ser Ser Asn Ile Ser Leu Arg Asn Asn Tyr Met Pro Ser Asn His Arg
165 170 175

Phe Gly Ser Ile Ala Ile Val Thr Phe Ser Pro Glu Tyr Ser Phe Arg
180 185 190

Phe Asn Asp Asn Cys Met Asn Glu Phe Ile Gln Asp Pro Ala Leu Thr
195 200 205

Leu Met His Glu Leu Ile His Ser Leu His Gly Leu Tyr Gly Ala Lys
210 215 220

Gly Ile Thr Thr Lys Tyr Thr Ile Thr Gln Lys Gln Asn Pro Leu Ile
225 230 235 240

-continued

```
Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Arg Thr Lys Phe Gln Val Lys Cys Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
    370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asp Asn Ile Asn
        435                 440                 445

Thr Pro Lys Glu Ile Asp Asp Thr Val Thr Ser Asn Asn Asn Tyr Glu
    450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
        515                 520                 525

Glu Gly Glu Asn Asn Val Asn Leu Thr Ser Ser Ile Asp Thr Ala Leu
    530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
                565                 570                 575

Gln Val Leu Val Asp Phe Thr Thr Glu Ala Asn Gln Lys Ser Thr Val
            580                 585                 590

Asp Lys Ile Ala Asp Ile Ser Ile Val Val Pro Tyr Ile Gly Leu Ala
        595                 600                 605

Leu Asn Ile Gly Asn Glu Ala Gln Lys Gly Asn Phe Lys Asp Ala Leu
    610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655
```

-continued

```
Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
    690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Ile Ile Asn Glu Val Lys Ile Asn Lys Leu Arg Glu Tyr
    770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys Arg Ile Lys Ser
        835                 840                 845

Ser Ser Val Leu Asn Met Arg Tyr Lys Asn Asp Lys Tyr Val Asp Thr
    850                 855                 860

Ser Gly Tyr Asp Ser Asn Ile Asn Ile Asn Gly Asp Val Tyr Lys Tyr
865                 870                 875                 880

Pro Thr Asn Lys Asn Gln Phe Gly Ile Tyr Asn Asp Lys Leu Ser Glu
                885                 890                 895

Val Asn Ile Ser Gln Asn Asp Tyr Ile Ile Tyr Asp Asn Lys Tyr Lys
            900                 905                 910

Asn Phe Ser Ile Ser Phe Trp Val Arg Ile Pro Asn Tyr Asp Asn Lys
        915                 920                 925

Ile Val Asn Val Asn Asn Glu Tyr Thr Ile Ile Asn Cys Met Arg Asp
    930                 935                 940

Asn Asn Ser Gly Trp Lys Val Ser Leu Asn His Asn Glu Ile Ile Trp
945                 950                 955                 960

Thr Phe Glu Asp Asn Arg Gly Ile Asn Gln Lys Leu Ala Phe Asn Tyr
                965                 970                 975

Gly Asn Ala Asn Gly Ile Ser Asp Tyr Ile Asn Lys Trp Ile Phe Val
            980                 985                 990

Thr Ile Thr Asn Asp Arg Leu Gly  Asp Ser Lys Leu Tyr  Ile Asn Gly
        995                 1000                1005

Asn Leu  Ile Asp Gln Lys Ser  Ile Leu Asn Leu Gly  Asn Ile His
    1010                 1015                 1020

Val Ser  Asp Asn Ile Leu Phe  Lys Ile Val Asn Cys  Ser Tyr Thr
    1025                 1030                 1035

Arg Tyr  Ile Gly Ile Arg Tyr  Phe Asn Ile Phe Asp  Lys Glu Leu
    1040                 1045                 1050
```

Asp Glu Thr Glu Ile Gln Thr Leu Tyr Ser Asn Glu Pro Asn Thr
1055 1060 1065

Asn Ile Leu Lys Asp Phe Trp Gly Asn Tyr Leu Leu Tyr Asp Lys
1070 1075 1080

Glu Tyr Tyr Leu Leu Asn Val Leu Lys Pro Asn Asn Phe Ile Asp
1085 1090 1095

Arg Arg Lys Asp Ser Thr Leu Ser Ile Asn Asn Ile Arg Ser Thr
1100 1105 1110

Ile Leu Leu Ala Asn Arg Leu Tyr Ser Gly Ile Lys Val Lys Ile
1115 1120 1125

Gln Arg Val Asn Asn Ser Ser Thr Asn Asp Asn Leu Val Arg Lys
1130 1135 1140

Asn Asp Gln Val Tyr Ile Asn Phe Val Ala Ser Lys Thr His Leu
1145 1150 1155

Phe Pro Leu Tyr Ala Asp Thr Ala Thr Thr Asn Lys Glu Lys Thr
1160 1165 1170

Ile Lys Ile Ser Ser Ser Gly Asn Arg Phe Asn Gln Val Val Val
1175 1180 1185

Met Asn Ser Val Gly Asn Cys Thr Met Asn Phe Lys Asn Asn Asn
1190 1195 1200

Gly Asn Asn Ile Gly Leu Leu Gly Phe Lys Ala Asp Thr Val Val
1205 1210 1215

Ala Ser Thr Trp Tyr Tyr Thr His Met Arg Asp His Thr Asn Ser
1220 1225 1230

Asn Gly Cys Phe Trp Asn Phe Ile Ser Glu Glu His Gly Trp Gln
1235 1240 1245

Glu Lys
1250

<210> SEQ ID NO 8
<211> LENGTH: 31
<212> TYPE: PRT
<213> ORGANISM: Clostridium botulinum

<400> SEQUENCE: 8

Met His Glu Leu Ile His Ser Leu His Gly Leu Tyr Gly Ala Lys Gly
1 5 10 15

Ile Thr Thr Lys Tyr Thr Ile Thr Gln Lys Gln Asn Pro Leu Ile
20 25 30

<210> SEQ ID NO 9
<211> LENGTH: 20
<212> TYPE: PRT
<213> ORGANISM: Homo sapiens

<400> SEQUENCE: 9

Met Gly Asn Glu Ile Asp Thr Gln Asn Arg Gln Ile Asp Arg Ile Met
1 5 10 15

Glu Lys Ala Asp
20

<210> SEQ ID NO 10
<211> LENGTH: 20
<212> TYPE: PRT
<213> ORGANISM: Homo sapiens -continued

<400> SEQUENCE: 10

Met Gly Asn Glu Ile Asp Ala Gln Asn Pro Gln Ile Lys Arg Ile Thr
1 5 10 15

Asp Lys Ala Asp
20

<210> SEQ ID NO 11
<211> LENGTH: 20
<212> TYPE: PRT
<213> ORGANISM: Homo sapiens

<400> SEQUENCE: 11

Ile Gly Asn Glu Ile Asp Ala Gln Asn Pro Gln Ile Lys Arg Ile Thr
1 5 10 15

Asp Lys Ala Asp
20

<210> SEQ ID NO 12
<211> LENGTH: 20
<212> TYPE: PRT
<213> ORGANISM: Homo sapiens

<400> SEQUENCE: 12

Ile Gly Asn Glu Ile Asp Ala Gln Asn Pro Gln Ile Lys Arg Ile Thr
1 5 10 15

Asp Lys Ala Asp
20

<210> SEQ ID NO 13
<211> LENGTH: 20
<212> TYPE: PRT
<213> ORGANISM: Homo sapiens

<400> SEQUENCE: 13

Met Gly Asn Glu Ile Asp Thr Gln Asn Arg Gln Ile Asp Arg Ile Met
1 5 10 15

Glu Lys Ala Asp
20

<210> SEQ ID NO 14
<211> LENGTH: 20
<212> TYPE: PRT
<213> ORGANISM: Homo sapiens

<400> SEQUENCE: 14

Met Gly Asn Glu Ile Asp Thr Gln Asn Arg Gln Ile Asp Arg Ile Met
1 5 10 15

Glu Lys Ala Asp
20

<210> SEQ ID NO 15
<211> LENGTH: 20
<212> TYPE: PRT
<213> ORGANISM: Homo sapiens

<400> SEQUENCE: 15

Met Gln Thr Glu Ile Glu Glu Gln Asp Asp Ile Leu Asp Arg Leu Thr
1 5 10 15

Thr Lys Val Asp
20

-continued

```
<210> SEQ ID NO 16
<211> LENGTH: 20
<212> TYPE: PRT
<213> ORGANISM: Homo sapiens

<400> SEQUENCE: 16

Ala Glu Ser Glu Leu Glu Arg Gln Asp Glu Ala Leu Asp Gly Val Ala
1               5                   10                  15

Ala Ala Val Asp
            20
```